United States Patent [19]

Garner et al.

[11] Patent Number: 5,094,531
[45] Date of Patent: Mar. 10, 1992

[54] SPECTROPHOTOMETER TO FLUOROMETER CONVERTER

[75] Inventors: Harold R. Garner, Encinitas; Larry S. Peranich, San Diego, both of Calif.

[73] Assignee: General Atomics, San Diego, Calif.

[21] Appl. No.: 520,041

[22] Filed: May 7, 1990

[51] Int. Cl.$^5$ .................. G01J 3/443; G01N 21/64
[52] U.S. Cl. ............................ 356/318; 356/73; 356/417; 250/458.1
[58] Field of Search .......... 250/365, 458.1, 459.1, 250/461.1, 461.2; 356/317, 318, 417, 73, 319, 323, 325

[56] References Cited

U.S. PATENT DOCUMENTS

| | | | |
|---|---|---|---|
| 2,381,414 | 8/1945 | Wilkie | 250/365 |
| 4,180,327 | 12/1979 | Maeda et al. | 356/325 |
| 4,305,660 | 12/1981 | Kallet | 356/73 |

FOREIGN PATENT DOCUMENTS 0263838 12/1985 Japan ............... 250/458.1

OTHER PUBLICATIONS

Farrand Spctrofluorometer (Brochure), Received U.S. Patent Office Nov. 17, 1965.
Hardy, IBM Technical Disclosure Bulletin, vol. 6, No. 10, Mar. 1964, pp. 104 and 105.

Primary Examiner—F. L. Evans
Attorney, Agent, or Firm—Nydegger & Associates

[57] ABSTRACT

A converter for using a spectrophotometer as a fluorometer includes a barrier for blocking the light in a collimated beam from reaching the detector of the spectrophotometer after this light has passed through and excited a sample material. A second detector is positioned to receive any fluorscence from the material which is emitted in a direction substantially perpendicular to the path of the collimated beam. A signal, generated by the second detector in response to fluorescence from the sample material, is modified to drive a second light source with an intensity which is linearlized relative to the generated signal. The detector of the spectrophotometer then receives the output from this second light source to measure the intensity of the fluorescence.

26 Claims, 2 Drawing Sheets

SPECTROPHOTOMETER TO FLUOROMETER CONVERTER

FIELD OF THE INVENTION

The device of the present invention pertains generally to diagnostic equipment. More particularly, the present invention pertains to devices which modify diagnostic equipment to interchangeably accomplish material quantization by alternative optical diagnostic techniques. The present invention is particularly, but not exclusively, useful for converting a spectrophotometer into a fluorometer.

BACKGROUND OF THE INVENTION

The quantization of a particular material is diagnostically useful in such diverse fields of technology as biology, chemistry and materials science. In particular, two of the more well known techniques for material quantization are spectrophotometry and fluorometry. It happens, however, that while both spectrophotometry and fluorometry involve procedures for the determination of specific optical characteristics of a material to be quantified, the phenomena observed by these procedures are significantly different.

In spectrophotometry, a beam of light is directed toward a sample of the material to be quantified, and the amount of light absorbed by this material at various light wavelengths as the light beam passes through it is measured to quantify the material. The spectrophotometer required to perform this technique typically includes very sensitive optical elements and is, consequently, quite expensive.

Fluorometry, in contrast to spectrophotometry, is based on the phenomenon whereby a material emits light of a characteristic wavelength when it is properly excited. Specifically, in fluorometry, molecules of a sample material are excited by absorbed light having a relatively short wavelength and, in response to this excitation, the molecules emit light at a relatively longer wavelength. Additionally, because of the basic differences in the underlying phenomena, fluorometers differ significantly from spectrophotometers. This is so in large part because a fluorometer must account for certain considerations which are not encountered during spectrophotometry. For instance, a fluorometer must be able to clearly differentiate the light which is emitted as fluorescence by the sample material from the light which is used to excite the material into its fluorescence. Further, the detecting elements of a fluorometer must have greater sensitivity than those used in a spectrophotometer in order to effectively sense the lower levels of light which typically result in fluorometry.

On the other hand, fluorometers and spectrophotometers do have some commonalities. Importantly, many components used in spectrophotometers are also used in fluorometers. Also, and not suprisingly, spectrophotometers and fluorometers can both be quite expensive.

In light of the above, it is an object of the present invention to provide a converter which effectively employs components in a spectrophotometer as components in a fluorometer. Another object of the present invention is to provide a converter which is relatively inexpensive. Still another object of the present invention is to provide a converter which is relatively easy to manufacture and comparatively cost-effective.

SUMMARY OF THE INVENTION

In accordance with the present invention, a device for converting a spectrophotometer into a fluorometer comprises components which function in combination with the optical elements of the spectrophotometer to change its operative diagnostic technique from the measuring of a material's light absorption characteristics (i.e. spectrophotometry) to the measuring of a material's fluorescence characteristics (i.e. fluorometry). The spectrophotometer, itself, is of standard construction and includes certain basic optical elements. These elements are: a light source for directing a beam of collimated light having selected wavelengths onto the material to be quantified; and a detector for analyzing the light which passes through the material.

In cooperation with a spectrophotometer as generally described above, the converter of the present invention includes an optical barrier which blocks the beam of collimated light after it has passed through the material. Specifically, this barrier prevents light in the beam from being incident on the detector of the spectrophotometer or on the detector of the fluorometer. The converter does, however, rely on the beam of collimated light to excite the material being analyzed and quantified.

The converter also includes its own detector, a second detector, which is positioned to receive the fluorescence from the material which is emitted in a direction that is substantially perpendicular to the axis of the beam of collimated light. Additionally, a monochromator, or a filter or other wavelength selective device, is positioned between the material and the second detector to select the desired wavelengths of light which can be received by the second detector.

Within the converter, a signal which is representative of the intensity of fluorescent light received by the second detector is generated and passed to associated electronic components for further processing. In the preferred embodiment of the present invention, this signal is processed by the electronic components to drive a second light source which is optically associated with the detector of the spectrophotometer. Specifically, for the preferred embodiment, light from this second light source activates the detector of the spectrophotometer to create a reading within the circuitry of the spectrophotometer which is proportional to the intensity of fluorescent light emitted by the material. Consequently, this reading is representative of the concentration of the material. To accomplish this, light from the second light source must be predictively proportional to the intensity of the fluorescence sensed by the second detector. The output intensity of the second light source, however, will not necessarily be linear in its response to an input. Therefore, the second light source is electronically and optically connected with the electronics of the second detector to provide feedback control that will establish the desired linear response for the second light source. It will be appreciated that with this combination, the components of a spectrophotometer may be effectively used as a fluorometer without being replaced In an alternate embodiment of the present invention, the detector of the spectrophotometer is not used for measuring the fluorescence of the material. Instead, the second detector is used for this purpose and additional components are electronically connected with the second detector to indicate the measured fluorescence.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
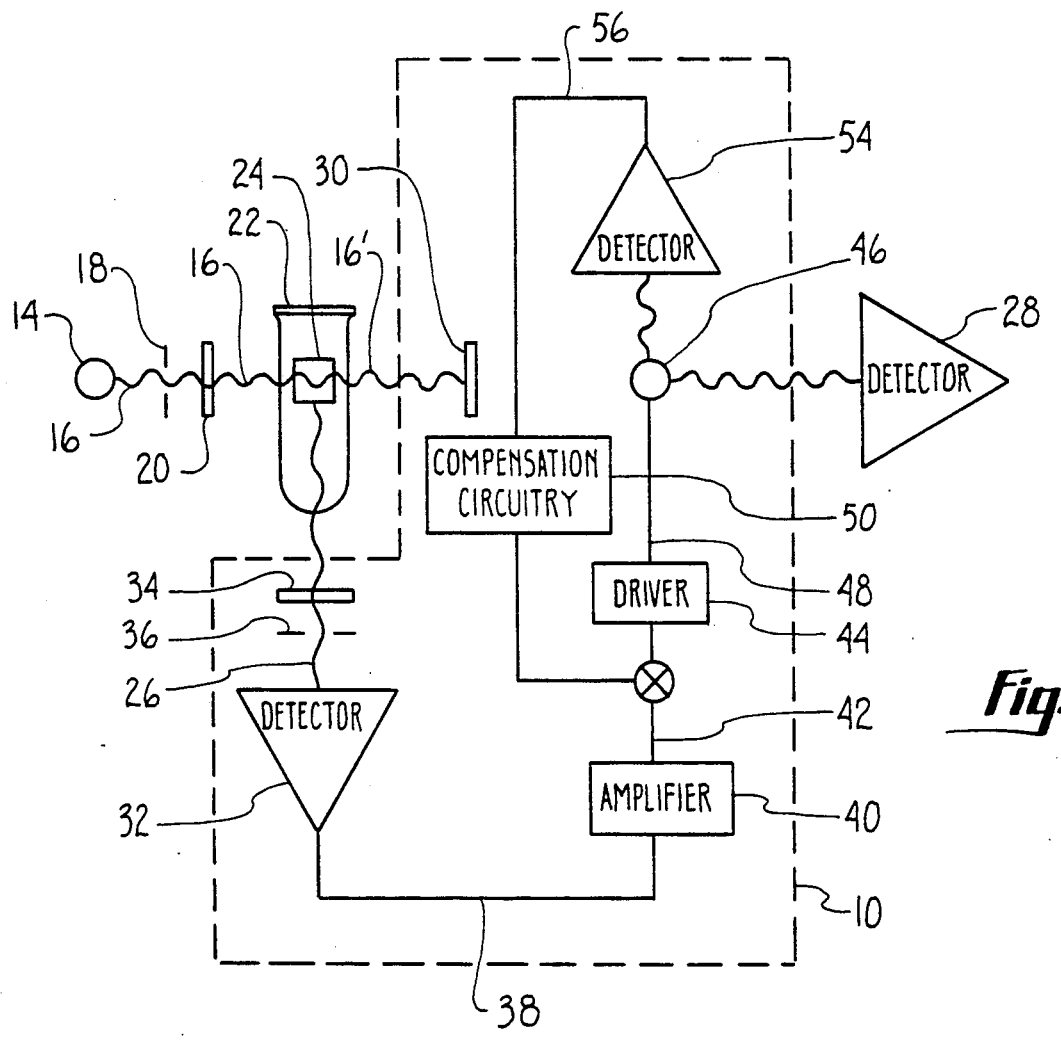
FIG. 1 is a schematic diagram showing the cooperative engagement of the converter of the present invention with a spectrophotometer to create a fluorometer.

Referring initially to FIG. 1, a converter, designated 10, for changing a spectrophotometer into a fluorometer in accordance with the present invention is schematically shown in its cooperation with a spectrophotometer. In order to better understand the cooperation of a converter 10 with a spectrophotometer, it is perhaps best to begin with a consideration of a spectrophotometer in isolation. For this purpose, reference is made to FIG. 2.

Figure 2:
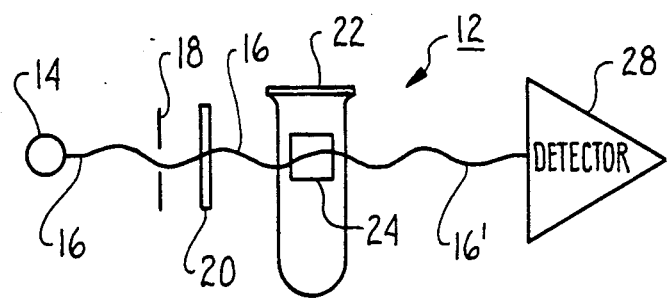
FIG. 2 is a schematic diagram of the essential components of a spectrophotometer.

In FIG. 2 it will be seen that a spectrophotometer, generally designated 12, includes a light source 14. As intended for the present invention, light source 14 may be of any type commonly used with spectrophotometers. Importantly, source 14 can generate broad spectrum light in both the visible and the ultraviolet ranges. A beam 16 of this light is shown radiating from light source 14. As shown, beam 16 is directed which causes the light in beam 16 to travel along substantially parallel paths. A filter 20 (or monochromator) is also provided in spectrophotometer 12 to pass only selected wavelengths of light in the beam 16. Consequently, as beam 16 emerges from filter 20, it is collimated and contains only preselected wavelengths. It happens, however, that some spectrophotometers position a filter (not shown) between material 24 and detector 28 rather than having a filter 20 as shown in FIG. 1. With such spectrophotometers, the filter 20 is eliminated and must, therefore, be replaced by an equivalent filter in converter 10.

A cuvette 22 for holding a sample of the material 24 to be measured and analyzed by spectrophotometer 12 is positioned on spectrophotometer 12 in the path of beam 16. In accordance with the well known phenomenon of spectrophotometry, the material 24 held within cuvette 22 will absorb some of the light in beam 16, depending on certain measurable characteristics of the material 24. The result of this is a modified beam 16' which is incident on the detector 28 that is placed behind cuvette 22 opposite light source 14. As will be readily appreciated by the skilled artisan, the above disclosure generally sets forth the essential components required for the operation of a spectrophotometer 12. With this in mind, reference is now made back to FIG. 1 to see just how such a spectrophotometer 12 can be changed by a converter 10 into a fluorometer.

Before turning to the structural components of converter 10, however, it is helpful to first understand some of the optical characteristics which are involved in the transformation of a spectrophotometer to a fluorometer. As indicated in FIG. 1, beam 16 is directed to be incident on material 24 regardless whether the device is to function as a spectrophotometer or a fluorometer. For fluorometry, however, beam 16 preferably comprises relatively high energy light having shorter wavelengths than the light emitted from material 24. If the material 24 is capable of emitting a fluorescence, molecules in the material 24 will be excited by this high energy beam 16 and subsequently emit the fluorescence as light having relatively lower energy levels and longer wavelengths. As is known, the fluorescence from a material 24 is isotropically radiated, and the emission beam 26 shown in FIG. 1 is but one example of this radiated emission. For reasons to be subsequently discussed, the emission beam 26, as shown, is specifically selected because it is radiated from material 24 in a direction which is substantially perpendicular to the path of the excitation beam 16 of collimated light.

FIG. 1 shows that converter 10 includes a barrier 30 between the material 24 and detector 28. Effectively, barrier 30 is so positioned to shield detector 28 from receiving light in beam 16'. Additionally, FIG. 1 shows that a detector 32 is positioned to receive light in beam 26 which is emitted from the material 24. Preferably, detector 32 is a photodiode of a type well known in the art. Alternatively, however, detector 32 can be a photomultiplier tube of a type which is also well known in the art. Additionally, detector 32 can be any other light amplification and detector system such as a microchannel plate connected to a photodiode or photomultiplier. In either case, the detector 32 is intended to generate a signal which is representative of the intensity of the light in emission beam 26. As indicated above, beam 26 is substantially perpendicular to beam 16. The detector 32 is positioned to establish this relationship in order to minimize the amount of stray light from beam 16 which might be incident on detector 32. Further, FIG. 1 shows that a filter 34 is positioned in the path of beam 26 between material 24 and detector 32 to pass only light of selected wavelengths from the material 24 to the detector 32. Optionally, a collimator 36 can also be positioned in the path of emission beam 26 substantially as shown.

In accordance with the present invention, the signal generated by detector 32 is passed to electronic components for further processing. Specifically, this signal is passed via line 38 to a high gain amplifier 40 and the output of amplifier 40 is transmitted via line 42 to a driver 44 which is connected to the light source 46 by a line 48. Accordingly, the illumination and the consequent intensity of the illumination of light source 46 is driven by the signal which is generated by detector 32. Although light source 46 may be of any type well known in the art, light source 46 is preferably a light emitting diode (LED).

As shown in FIG. 1, the light source 46 of converter 10 is positioned to radiate light onto detector 28. Thus, because the light from light source 46 is a consequence of the signal which is generated by detector 32 in response to fluorescence from material 24, the detector 28 of spectrophotometer 12, in effect, becomes the detector of a fluorometer. When light source 46 is a light emitting diode, the illumination from source 46 is not linearly proportional to the signal generated by the detector 32. Consequently, some feedback control for light source 46 is required in order to linearize the output of source 46. As shown in FIG. 1, this can be accomplished by providing well known feedback control.

Specifically, a detector 54 is positioned to receive light from source 46 and generate a signal which is transmitted over line 56 to circuitry in block 50. With this signal, the circuitry of block 50 adjusts the output of driver 44 to linearize the illumination of light source 46 with the output signal from detector 32.

Figure 3:
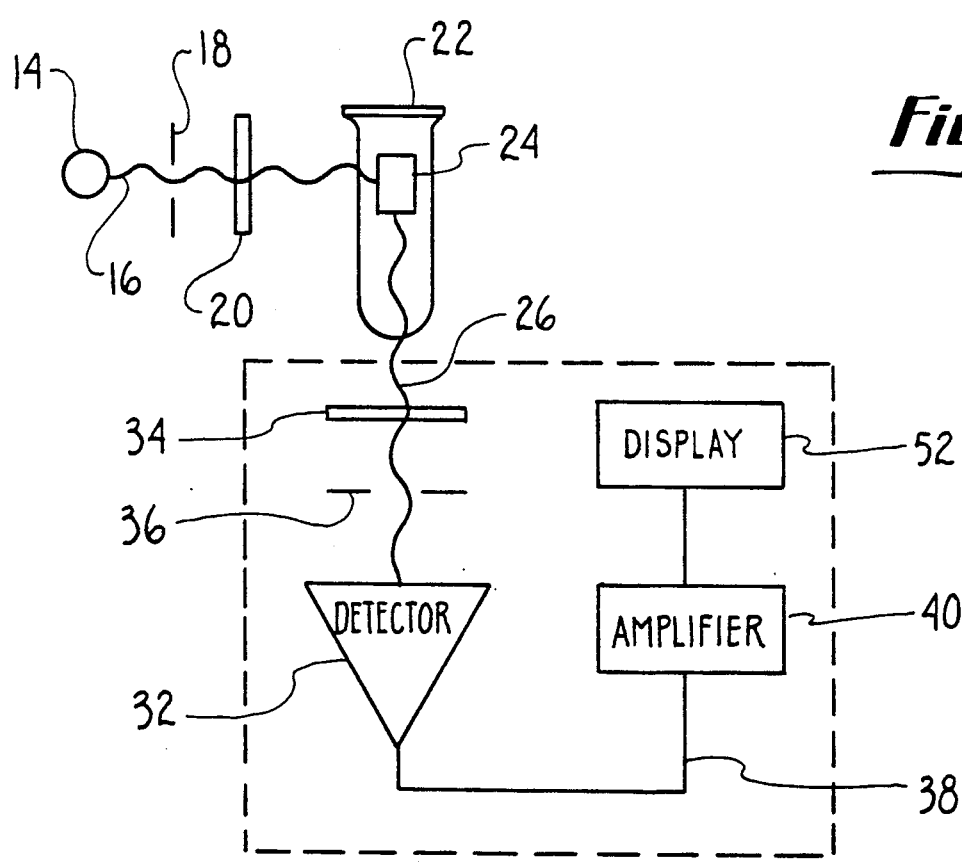
FIG. 3 is a schematic diagram of an alternate embodiment of the converter of the present invention in its cooperation with a spectrophotometer.

In an alternate embodiment of the present invention as shown in FIG. 3, converter 10 can be modified to eliminate light source 46 and the associated components which allow source 46 to effectively interact with detector 28. Instead, a display 52 can be electronically connected with amplifier 40 to give direct readings of the signal generated by the detector 32.

OPERATION

In the operation of the present invention a cuvette 12 containing the sample material 24 to be measured and quantified is placed in a spectrophotometer 12. The converter 10 is then positioned on the spectrophotometer 12 with the barrier 30 between light source 14 and detector 28. Light in beam 16 from light source 14 is collimated by slit 18 and filtered by wavelength filter 20 before it is incident on material 24. As intended for the present invention, material 24 is excited by beam 16 and is caused to isotropically emit a fluorescence. The portion of this fluorescence which radiates as a beam 26 from material 24 in a direction substantially perpendicular to the path of the collimated excitation beam 16 is filtered by a wavelength filter 34 and subsequently passed toward the detector 32. A signal, representative of the intensity of the fluorescence from material 24, is generated by the detector 32 and transmitted to electronic componentry for further processing.

In the preferred embodiment, an amplifier 40 takes the signal from detector 32 and uses it, with an appropriate feedback control, to drive a light source 46. Illumination from this light source 46 is then used to activate the detector 28 to provide measurements of the fluorescence from material 24. In an alternate embodiment of the present invention, the measurement of fluorescence from material 24 may be made directly from the detector 32 through appropriate electronic componentry and shown on the display 52.

While the particular spectrophotometer to fluorometer converter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A device for converting a spectrophotometer having a source for generating a beam of collimated light for illuminating a sample material and a detector for determining the light absorption characteristics of the material into a fluorometer having a detector for determining the fluorescence of the material which comprises:

a barrier for blocking light in said beam which has passed through said material from being incident on said detector of said spectrophotometer;

means for positioning said detector of said fluorometer to receive light which is fluorescently emitted from said material; and means for communicatively engaging said detector of said fluorometer and said detector of said spectrophotometer.

2. A device as recited in claim 1 further comprising means positioned between said material and said detector of wavelengths of light emitted from said material.

3. A device as recited in claim 1 wherein said detector of said fluorescence is positioned to receive light which is fluorescently emitted from said material in a direction substantially perpendicular to said beam.

4. A device as recited in claim 1 further comprising a second light source electrically connected to said detector of said fluorometer and responsive thereto for generating light with an intensity that is representative of the light received by said detector of said fluorometer.

5. A device as recited in claim 4 wherein said second light source is a light emitting diode and said device further comprises electronic feedback means connected between said second light source and said detector of said fluorometer to establish a linearized response for said second light source.

6. A device as recited in claim 5 wherein light from said second light source is directed toward said detector of said spectrophotometer and said detector of said spectrophotometer is used for determining the fluorescence of said material.

7. A device as recited in claim 1 wherein said detector of said spectrophotometer is a photodiode.

8. A device as recited in claim 1 wherein said detector of said fluorometer is a photodiode.

9. A device as recited in claim 2 wherein said means for selectively passing predetermined wavelengths of light is a filter.

10. A device as recited in claim 2 wherein said means for selectively passing predetermined wavelengths of light is a monochromator.

11. A device as recited in claim 1 further comprising means for selectively passing predetermined wavelengths of light in said beam.

12. A device for use in combination with the detector and the light source of a spectrophotometer to measure the fluorescence of a material which is excited by a beam of collimated light from the light source which comprises:

means positioned between said material and said detector for blocking light in said beam which has passed through said material from being incident on said detector;

means for detecting light which is fluorescently emitted from said material; and means responsive to said detecting means for activating said detector to generate a signal that is representative of the fluorescence of said material.

13. A device as recited in claim 12 wherein said detecting means detects light which is fluorescently emitted from said material in a direction substantially perpendicular to said beam.

14. A device as recited in claim 12 wherein said blocking means is a light absorbing barrier.

15. A device as recited in claim 12 wherein said detecting means is a photodiode.

16. A device as recited in claim 12 further comprising means positioned between said material and said detecting means for selectively passing predetermined wavelengths of light emitted from said material.

17. A device as recited in claim 12 wherein said activating means comprises a second light source electrically connected to said detecting means and responsive thereto for generating light with an intensity that is representative of the light received by said detecting means and said second light source is directed toward said detector.

18. A device as recited in claim 17 wherein said second light source is a light emitting diode and said device further comprises electronic feedback means connected between said second light source and said detecting means to establish a linearized response for said second light source.

19. A device as recited in claim 12 wherein said detector of said spectrophotometer is a photodiode.

20. A device as recited in claim 16 wherein said means for selectively passing predetermined wavelengths of light is a filter.

21. A device as recited in claim 16, wherein said means for selectively passing predetermined wavelengths of light is a monochromator.

22. A device as recited in claim 13 further comprising means for selectively passing predetermined wavelengths of light in said beam.

23. A method for using a spectrophotometer having a light source and a light detector as a fluorometer which comprises the steps of:

exciting a sample material with an excitation beam of collimated light generated by said light source of said spectrophotometer;

filtering fluorescent light from said sample material to form an emission beam traveling on a path which is substantially perpendicular to the path of said excitation beam to minimize interference of said emission beam by said excitation beam;

detecting said emission beam to generate a signal which is representative of the intensity of the fluorescence from said material; and converting said signal into a light beam directed at said light detector of said spectrophotometer.

24. A method as recited in claim 23 wherein said excitation beam comprises selected wavelengths.

25. A method as recited in claim 22 further comprising the steps of:

blocking light in said excitation beam from being incident on the detector of said spectrophotometer; and driving a second light source with said signal to activate said light detector of said spectrophotometer.

26. A method as recited in claim 25 further comprising the step of modifying said signal with feedback control to linearize the output of said second light source in response to said generated signal.

* * * * *